United States Patent [19]

Weil et al.

[11] Patent Number: 5,195,942
[45] Date of Patent: Mar. 23, 1993

[54] CARDIAC ARREST TREATMENT

[75] Inventors: Max H. Weil, Northbrook; Jose Bisera, Lake Bluff, both of Ill.

[73] Assignee: Institute of Critical Care Medicine, Palm Springs, Calif.

[21] Appl. No.: 744,082

[22] Filed: Aug. 12, 1991

[51] Int. Cl.⁵ .............................................. A61M 29/02
[52] U.S. Cl. ........................................ 600/18; 600/16;
606/194; 604/67; 604/96; 604/101; 604/53
[58] Field of Search ............................ 600/16, 17, 18;
128/419 D; 604/99, 100, 101, 67, 96, 52, 53;
606/194

[56] References Cited

U.S. PATENT DOCUMENTS

| | | | |
|---|---|---|---|
| 4,527,549 | 7/1985 | Gabbay | 600/18 |
| 4,531,936 | 7/1985 | Gordon | 600/18 |
| 4,697,574 | 10/1987 | Karcher et al. | 600/18 |
| 5,024,668 | 6/1991 | Peters et al. | 600/18 |

OTHER PUBLICATIONS

Cardiac Resuscitation by Extracorporeal Circulation After Failure of Conventional CPR by Raul J. Gaxmuri et al, Jul., 1991, pp. 65-73.
Effect of Continuous Intra-Aortic Balloon Inflation in Canine Open Chest Cardiopulmonary Resuscitation by Robert C. Weley, Jr. et al, 1990, vol. 18, No. 6 pp. 630-633.

Primary Examiner—William E. Kamm
Assistant Examiner—George Manuel
Attorney, Agent, or Firm—Arthur Freilich; Robert D. Hornbaker; Leon D. Rosen

[57] ABSTRACT

A method and apparatus are described for resuscitating a person who has suffered cardiac arrest. The method includes threading a balloon through the aorta until it lies along the ascending aorta, and then inflating the balloon (40, FIG. 1) to block the ascending aorta to thereby increase blood flow into the coronary arteries (30, 32). A tube (42) extends through the balloon, and blood-compatible fluid which is preferable oxygen rich, is injected past the balloon to provide additional oxygen-carrying fluid to flow through the coronary arteries when the balloon is inflated. The balloon is repeatedly deflated and inflated, so after a period of perhaps 30 seconds during which blood flows only to the coronary arteries, the balloon is deflated to allow some blood flow to the brain. During the entire procedure, pressure is repeatedly applied to the chest and therefore to the heart to sustain blood circulation.

17 Claims, 2 Drawing Sheets

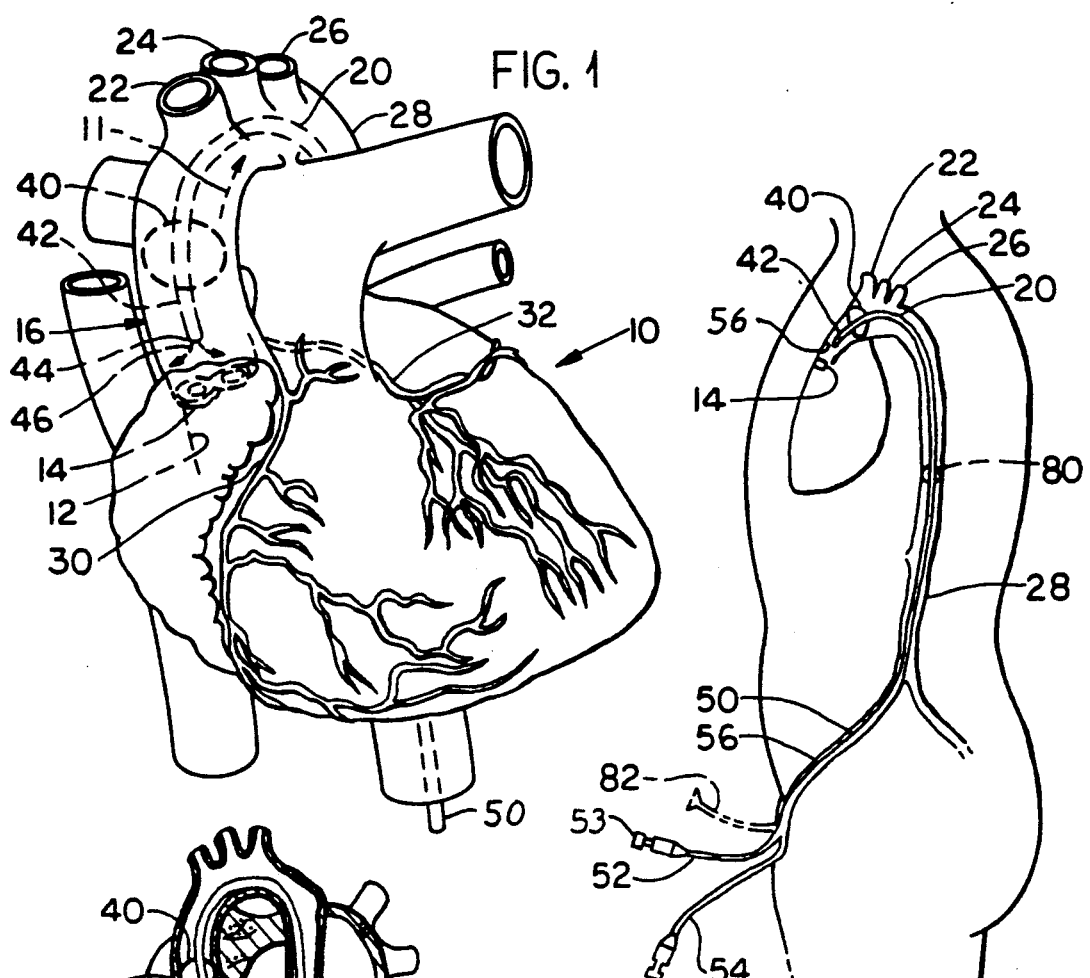
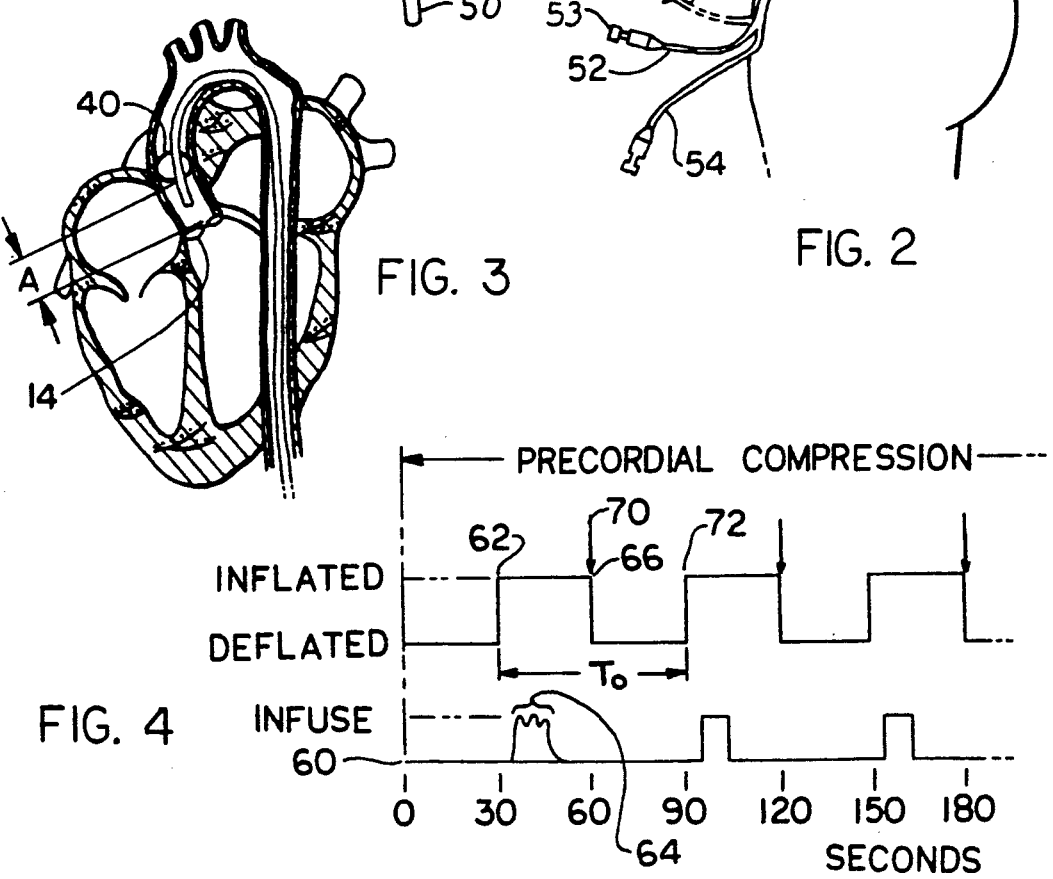

CARDIAC ARREST TREATMENT

BACKGROUND OF THE INVENTION

Current techniques of closed-chest cardiac resuscitation include repeatedly applying pressure to the chest, to thereby repeatedly apply pressure to the heart to cause ejection of blood and thereby partially sustain blood circulation to vital organs. Although blood flow to various parts of the body is necessary for survival, with blood flow to the brain without long interruption being especially important, blood flow to the coronary arteries is critical. Blood flow to the coronary arteries can help restart normal pumping operation of the heart, so that the rest of the body is supplied with blood. Current techniques of closed-chest cardiac resuscitation generate blood flow which usually does not exceed 25 percent of normal flow. As a result, the coronary perfusion pressure (aortic pressure minus right atrium pressure at the same time during diastole) is relatively low. It has been demonstrated that coronary perfusion pressure of 15 mmHg is required for successful restoration of spontaneous circulation with external defibrillation. Increases in coronary perfusion pressure exceeding 25 mmHg increase resuscitability to more than 80 percent. A technique which increases coronary perfusion pressure to thereby increase blood flow to the coronary arteries, would be of great value in resuscitation after cardiac arrest.

SUMMARY OF THE INVENTION

In accordance with one embodiment of the present invention, a method and apparatus are provided for resuscitating a person or other mammal who has suffered cardiac arrest. The method includes blocking flow in a normal downstream direction through the ascending aorta while encouraging pumping by the heart, so a high proportion of fluid pumped by the heart passes into the coronary arteries to restore the blood supply to the heart muscles. A blood-compatible fluid (preferably oxygen rich) is preferably injected into the space between the blockage and the aortic valve, to increase available fluid and pressure to flow through the coronary arteries. The blockage is preferably relieved at intervals, so that some fluid can flow to the brain. A location along the ascending aorta also can be blocked so when fluid is allowed to flow to the brain as well as the coronary arteries, little fluid flows to other parts of the body.

Apparatus for resuscitating can include a catheter having an inflatable balloon of a size to block the ascending aorta when inflated. A conduit extends through the balloon and has an open distal end so a blood-compatible fluid, preferably enriched with oxygen, can be injected through the tube. A control circuit can be connected to a source of blood-compatible fluid and a source of pressured gas for inflating the balloon, to repeatedly inflate the balloon and inject oxygen-carrying fluid after each inflation, with each inflation being followed by a deflation to allow blood flow to the brain.

The novel features of the invention are set forth with particularity in the appended claims. The invention will be best understood from the following description when read in conjunction with the accompanying drawings.

BRIEF DESCRIPTION OF THE DRAWINGS

FIG. 1 is an isometric view of the heart of a person, with a catheter assembly installed therein.

FIG. 2 is a partial side view of a body of a person, showing a catheter with balloon expanded in the ascending aorta and also showing in phantom lines a second balloon that can be used along the descending aorta.

FIG. 3 is a simplified sectional front view of the heart of FIG. 2.

FIG. 4 includes graphs showing steps in the process of the invention, indicating the times during which different steps are taken.

DESCRIPTION OF THE PREFERRED EMBODIMENTS

Figure 6:
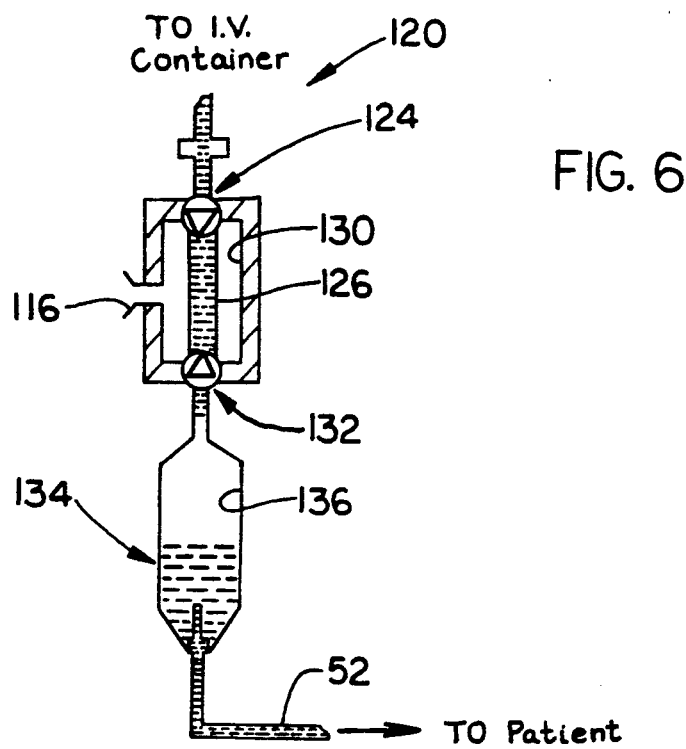
FIG. 6 is a partial view of the apparatus of FIG. 5, showing the liquid injecting apparatus.

FIG. 1 illustrates parts of the heart 10. Oxygen rich blood is pumped from the left ventricle 12 in a downstream direction 11 through the aortic valve 14 into the ascending aorta 16. The ascending aorta 16 extends to the aortic arch 20 which branches into three arteries that comprise the brachiocephalic innominate artery 22 that carries blood to the neck and head, the left carotid artery 24 that carries blood to the head, and the left subclavian artery 26 that carries blood to the arms. The aortic arch 20 connects to the descending aorta 28 that carries blood largely downwardly to other parts of the body. The muscles of the heart are fed oxygen and nutrients through the right and left coronary arteries 30, 32 which receive blood from the lower portion of the ascending aorta 16. About five percent of the blood pumped by the heart (into the ascending aorta 16) flows to the coronary arteries.

Current techniques of closed-chest cardiac resuscitation include repeatedly applying pressure to the chest to cause some compression and expansion of the heart so as to cause some pumping of the blood. Also, a defibrillation machine may be used to apply current pulses in an attempt to restore the rhythm of a fibrillating heart. These techniques often result in some pumping of blood to the body, but with the volume output often being much lower than normal and sometimes being insufficient to restore spontaneous circulation.

In accordance with the present invention, applicant blocks the ascending aorta, as with the inflated balloon shown at 40. With steps taken to cause blood flowing, as by repeated application of pressure (each followed by relaxation) to the chest, the blood that is pumped out of the left ventricle 12 through the aortic valve 12 into the ascending aorta 16, is all directed into the coronary arteries 30, 32 that branch from the lower portion of the ascending aorta. Such blockage prevents the small amount of pumped blood from reaching other organs of the body. However, the pumping of maximum amounts of blood into the coronary arteries provides maximum oxygen and other nourishment (as well as removal of carbon dioxide and other waste) to the cardiac muscles to restore their functioning at an early time. Of course, once the heart muscles are able to pump, the blockage can be removed and all parts of the body can receive blood pumped in a normal manner from the heart.

Applicant also provides a tube 42 that extends through and beyond the balloon 40, and which has an open distal end 44 through which a blood-compatible fluid can be injected. The blood-compatible fluid is preferably oxygen rich. After blocking the ascending aorta as with the balloon 40, applicant injects the blood-compatible fluid 46 into the space between the aortic valve 14 and the inflated balloon 40. The injected fluid increases the pressure downstream of the aortic valve, to increase the pressure of fluid thereat and the perfusion pressure, to enhance flow through the coronary arteries.

FIG. 2 illustrates one manner in which the balloon 40 can be installed and inflated and fluid injected through the tube 42. A catheter 50 includes a first conduit 52 with a syringe coupling 53, that extends through the balloon 40 and that ends in the tube 42. The catheter also includes a second or inflation tube 54 with a second syringe coupling 55, that connects to the balloon 40 and which can receive pressured fluid (usually gas) to inflate the balloon. With the balloon deflated, the catheter is inserted into the femoral artery 56 and threaded therethrough and into the descending aorta 28. The catheter can be instead inserted into the carotid axillary artery, into the aorta. The tube is threaded through the aortic arch 20 into the ascending aorta. The balloon is preferably positioned at a distance A (FIG. 3) of three to five centimeters downstream (along the direction of normal blood flow 11) from the aortic valve 14. After the catheter is installed, a syringe can be coupled to the inflation tube 54 (FIG. 2) to inject gas such as air into the inflation tube to blow up the balloon so as to block the ascending aorta. Immediately thereafter, an oxygen-containing fluid such as oxygen-rich blood or other blood-compatible fluid is injected into the first conduit 52 to flow out through the tube 42 into the upstream portion 56 of the ascending aorta to increase flow into the coronary arteries.

FIG. 4 illustrates the times at which various steps can be performed to enhance resuscitation. The procedure is shown as beginning at a "O" time indicated at 60, where the balloon is deflated, and only precordial compression is administered, as by repeatedly compressing and releasing the chest of the patient. At the 30 second time, at 62, the balloon is inflated. Immediately thereafter, during the period 64, the oxygen-containing blood-compatible fluid is injected through the tube 16 into the lower portion of the ascending aorta, upstream from the balloon. It may be noted that, while it is preferable to insert oxygen-containing fluid, it is also possible to insert any blood compatible fluid merely to increase the pressure to enhance blood flow into the coronary arteries. At the time indicated at 66, the balloon has been inflated for 30 seconds and the balloon is deflated. Such deflation is provided to enable some blood to flow to the brain to prevent damage to the brain for lack of oxygen (and some nutrients and waste removal). Immediately prior to or after deflation of the balloon, at the time 70, defibrillation is attempted, as by applying high voltage current pulses to the chest in an effort to restore a workable rhythm to the heart muscles. At the time indicated at 72, the balloon is inflated again and oxygen-rich blood-compatible fluid is again injected upstream from the inflated balloon. This procedure continues with cycle times $T_o$ of one minute each. Of course, the particular time during which the balloon is inflated and deflated can be varied, although it is desirable to have the balloon inflated no more than about 2.5 minutes at a time, to minimize damage to the brain.

Referring to FIG. 2, the figure indicates a possible second balloon 80 and a second inflation tube 82 as part of the catheter. The second balloon 80 lies along the descending aorta 28 and can be used to block it. This assures that, when the first balloon 40 is deflated to allow blood to flow to the brain, that the blood will not flow to the lower parts of the body and therefore reduce the amount of blood to the brain. It might be possible to block the left subclavian artery 26 to prevent some of the blood from flowing to the arms, but since this is so close to the left carotid artery 24, this is very difficult to do. With the second balloon 80 utilized, the second balloon 80 is inflated and remains inflated during times when the first balloon 40 is inflated and then deflated. Of course, after a few minutes, the second balloon 80 may be deflated to allow some blood flow to the rest of the body.

Figure 5:
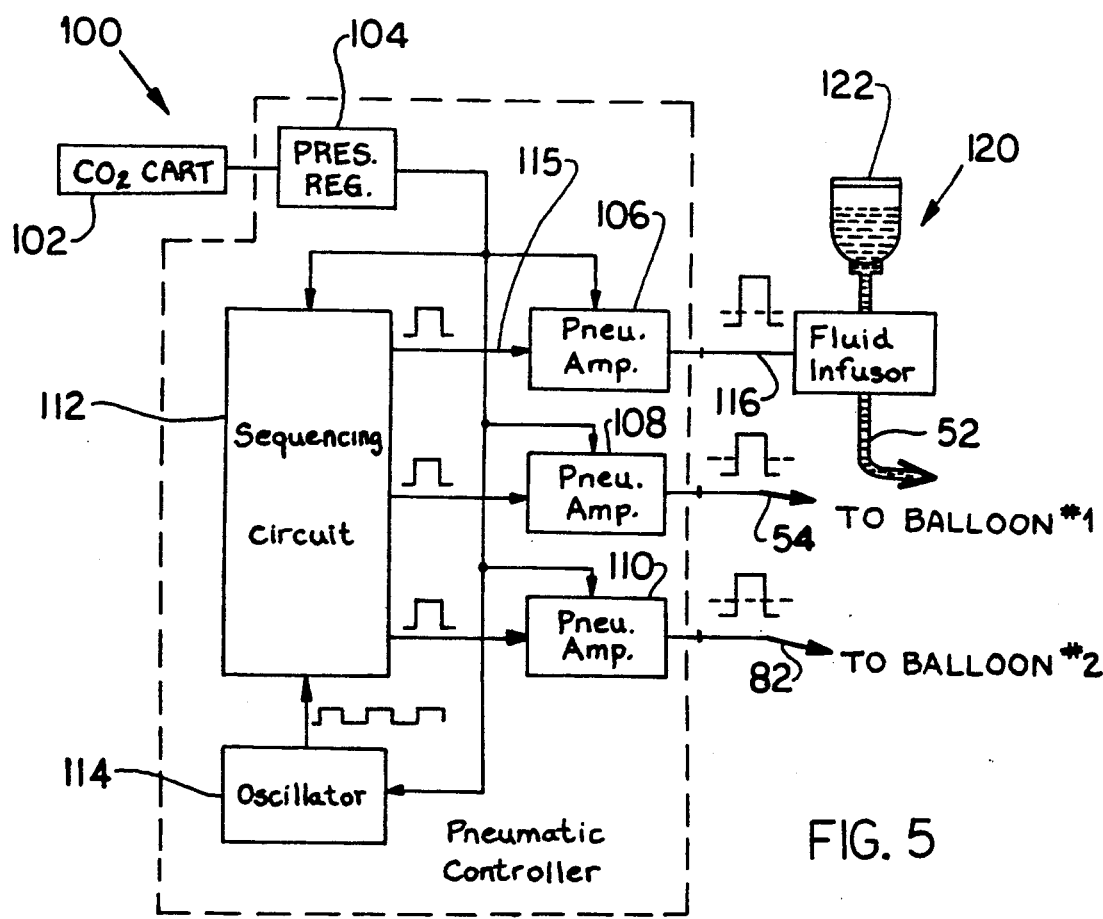
FIG. 5 is a block diagram view of an automated apparatus for conducting the procedure indicated in FIG. 4.

FIGS. 5 and 6 illustrate an apparatus 100 that can be connected to the proximal end of the catheter to automatically inflate and deflate the balloon lying in the ascending aorta, and to inject blood-compatible fluid into the lower portion of the ascending aorta after each balloon inflation. The apparatus includes a carbon dioxide cartridge 102 whose high pressure passes through a pressure regulator 104 that maintains a constant pressure output. The output of the pressure regulator is delivered to three pneumatic amplifiers 106, 108, and 110. Each of the amplifiers is controlled by a sequencing circuit 112 whose timing is established by an oscillator 114. The sequencing circuit 112 delivers signals, such as electrical currents, to the amplifiers 106–110 to turn them on and off. During the operation of the apparatus, the sequencing circuit 112 delivers signals to the pneumatic amplifiers 108 and 110 that extend to the inflation tubes 54, 82 to inflate both balloons 40, 80. A short time after inflation of a balloon 40, a sequence of signals are sent from the sequencing circuit over line 115 to amplifier 106. This causes the amplifier to deliver a sequence of carbon dioxide pressure pulses over line 116 to a fluid injector 120 that connects an IV (intravenous) container 122 to the first conduit 52 that carries blood-compatible fluid to the lower part of the ascending aorta.

FIG. 6 illustrates details of the fluid injector 120. Blood-compatible fluid from the IV container passes through a check valve 124 to a flexible compressible tube 126. When pulses of pressured carbon dioxide are delivered over line 116, they enter a chamber 130 surrounding the compressible tube 126 to compress the tube 126. The compressed tube causes the outflow of its contents through a pressure relief valve 132 to an accumulator chamber 134. Thus, immediately after the balloon 40 is inflated, a series of pressure pulses is delivered over line 116 to the chamber 130 to cause the blood compatible fluid to flow in pulses into the accumulator chamber 134. The upper portion 136 contains a gas which is compressed as the accumulator chamber fills with liquid, to press the liquid through the first tube 52 of the catheter so as to flow to the bottom of the ascending aorta. After several seconds of delivery of pulses over line 116, the pulses stop, and the flow of fluid out of the accumulator chamber 134 decreases over the next few seconds.

Applicants have injected blood into the ascending aorta to resuscitate a group of rats, utilizing blood from a donor rat. Applicants found that the above method allowed cardiac resuscitation after prolonged cardiac arrest of eight minutes or more, after conventional methods failed. Subsequent tests on pigs demonstrated that the combination of ascending aorta occlusion (blockage) and injection is highly effective after more than 15 minutes of cardiac arrest. Occlusion of the ascending aorta in association with precordial compression increases perfusion pressure to levels that are three or more times those achieved with precordial compression alone. The coronary perfusion pressure was increased from less than 15 mmHg prior to inflation of the balloon 40 lying in the ascending aorta, to more than 70 mmHg after balloon inflation. Of course, such obstruction must be intermittent to allow some flow to the brain arteries to allow survival of the brain. When injection of fluid was combined with intermittent balloon (40) obstruction and precordial compression, the coronary profusion pressure was increased to more than 150 mmHg with correspondingly greater resuscitability and 72 hours survival with minimal or absence of neurological (brain) deficit.

The aortic occlusion catheter 50 can be inserted through the femoral artery and along the aorta until the balloon is about three to five centimeters distal to the aortic valve. After 30 seconds of precordial compression the balloon is inflated to block the aorta, which is immediately followed by the infusion of between 20 and 50 milliliters of blood or other blood-compatible fluid. After 30 seconds of occlusion of the ascending aorta, and immediately (within about 3 seconds) prior to or after deflation of the balloon, defibrillation is attempted. This sequence of balloon inflation, fluid infusion, balloon deflation, and defibrillation, is repeated, with the exception that defibrillation is performed only if ventricular fibrillation persists, rather than electromechanical dissociation. Electromechanical dissociation is defined as an adequate cardiac rhythm but no effective cardiac pump action by the heart, so that no significant arterial (aortic) pressure is generated spontaneously. In tests on pigs having a weight of 40 kg, first defibrillation was attempted after seven minutes of cardiac arrest caused by ventricular fibrillation, which resulted in electromechanical dissociation. After a balloon inflation 40 in the proximal aorta (ascending aorta) and injection of 30 ml of oxygen enriched physiological salt solution, electromechanical dissociation was converted to ventricular fibrillation within an additional 10 to 14 minutes. A total of between 300 and 450 ml of fluid was injected, and ventricular fibrillation was then successfully reverted by electrical counter shock to a regular rhythm with restoration of spontaneous circulation, that is, successful cardiac resuscitation. Similar amounts of blood-compatible fluid should be injected into persons of a similar weight (40 kg or 90 pounds) with increased amounts of fluid for heavier persons. Inflation and deflation of the balloon and fluid injection can be accomplished using the apparatus of FIG. 2 with the aid of 50 milliliter syringes, which apply pressures ranging from 100 to 300 mmHg.

Thus, the invention provides a method and apparatus for resuscitating a person or other mammal who has suffered cardiac arrest. The method includes occlusion of the ascending aorta, preferably accompanied by precordial compression as by compression of the chest i.e. by means external to patient. This causes any blood that is pumped, together with any injected blood-compatible fluid, to flow into the coronary arteries to allow the heart to recover function as soon as possible. The blood compatible fluid which is injected into the ascending aorta upstream from the balloon in combination with the balloon obstruction, strikingly increases the pressure thereat. The occlusion of the ascending aorta is halted at periods of less than 2.5 minutes each, and preferably after periods of about 30 seconds of occlusion, to allow blood flow to the brain. It is noted that heartbeats normally occur at a rate that is generally 70 or more beats per minute. Blood flow to the brain can be enhanced by occlusion of the descending aorta, as by the use of a second balloon that is inflated in the descending aorta.

Although particular embodiments of the invention have been described and illustrated herein, it is recognized that modifications and variations may readily occur to those skilled in the art, and consequently, it is intended that the claims be interpreted to cover such modifications and equivalents.

We claim:

1. A method for resuscitating a person or other mammal who has suffered cardiac arrest, comprising:
   blocking a majority of the flow of blood from the heart in a normal downstream direction from the left ventricle through the ascending aorta, and using means external to the patient to cause compression of the heart, to thereby direct a high portion of flow into the coronary arteries.

2. The method described in claim 1 wherein:
   said step of using means external to the patient to cause compression of the heart includes applying pressure to the chest at least while blocking said flow.

3. The method described in claim 1 including:
   injecting oxygen-rich blood-compatible fluid through a conduit lying in the ascending aorta and past the location of blockage, while performing said step of blocking and substantially while performing said step of using means to cause compression, to encourage fluid flow toward the coronary arteries.

4. The method described in claim 1 including:
   at intervals of less than 2.5 minutes, ending said step of blocking flow, to allow flow through the ascending aorta to the brain.

5. The method described in claim 4 including:
   blocking the descending aorta at least some of the time after ending said step of blocking flow through the ascending aorta, to direct a high proportion of flow to the brain.

6. The method described in claim 1 wherein:
   said step of blocking is continued for a period of more than one second.

7. The method described in claim 1 wherein:
   said period during which the flow of blood through the ascending aorta is blocked, is on the order of 30 seconds.

8. The apparatus described in claim 7 wherein:
   said mechanism includes a conduit extending to a location between where the ascending aorta is blocked and a location along the coronary arteries, a container for holding oxygen-rich fluid, an da pumping device connected to said container and conduit;
   said control circuit is coupled to said pumping device to operate it to pump said oxygen-rich fluid at least some of the time when said control circuit is operating said mechanism to block the ascending aorta.

9. The apparatus described in claim 7 wherein:
   said mechanism is constructed to block substantially all flow of blood through the ascending aorta when operated to block, and to allow most of the flow into the ascending aorta to flow therethrough when operated to unblock;

said control circuit is constructed to operate said mechanism to unblock after a period of less than 2.5 minutes after the beginning of each operation of said mechanism to block.

10. The apparatus described in claim 7 wherein:

said control circuit is constructed to again operate said mechanism to again reduce the blockage of the ascending aorta after again blocking it;

said mechanism has a second portion which is operable to at least partially block and unblock the descending aorta;

said control circuit is constructed to operate said second portion to block the descending aorta, to allow substantial blood flow to the brain, during at least one of said periods when said control circuit operates said mechanism to unblock the ascending aorta.

11. Apparatus for use in resuscitating a person who has suffered cardiac arrest, comprising:

a catheter having an inflatable balloon of a size to block the ascending aorta of the person when inflated, a blood compatible fluid-carrying conduit extending through said balloon and having an open distal end and having a proximal end for receiving liquid, and an inflation conduit extending to said balloon to pass fluid thereto that inflates said balloon with said inflation conduit having a proximal end distant from said balloon;

a first source of blood compatible fluid;

a second source of pressured inflation fluid;

a first coupling for connecting said first source to said proximal end of said fluid-carrying conduit to cause fluid injection;

a second coupling for connecting said second source to said proximal end of said inflation conduit to inflate said balloon and allow deflation of said balloon;

a control circuit coupled to said first and second couplings, said circuit being constructed to operate said second coupling to repeatedly inflate said balloon, each time keeping said balloon inflated for a duration of a plurality of seconds, and to deflate said balloon after each of said durations of a plurality of seconds when said balloon has been kept inflated;

said control circuit also operating said second coupling to cause fluid injection of said oxygen-carrying blood compatible fluid at times when said balloon is inflated.

12. A method for resuscitating a person or other mammal who has suffered cardiac arrest, comprising:

threading a catheter having a distal end that includes an inflatable balloon and a tube extending beyond the balloon, up through the ascending aorta and past the top of the aortic arch and downwardly into the ascending aorta to a location upstream from the aortic valve;

repeatedly performing the steps of inflating said balloon and keeping said balloon inflated continually for a period of a plurality of seconds to block the ascending aorta during said period, and injecting a blood-compatible fluid through said tube to inject said fluid into a location upstream from said balloon but downstream from the aortic valve during said period when said balloon is inflated to increase fluid flow in the coronary arteries, and then deflating said balloon to allow blood to flow through the ascending aorta toward the brain.

13. The method described in claim 12 wherein:

said step of injecting blood-compatible fluid includes injecting oxygen-rich fluid.

14. The method described in claim 12 including:

repeatedly applying and relaxing pressure on the heart both when said balloon is inflated and when it is not inflated.

15. The method described in claim 12 including:

defibrillating the heart immediately after deflation of said balloon.

16. The method described in claim 12 wherein:

said catheter includes a second balloon, and said step of threading includes threading said second balloon through part of the descending aorta to a location downstream from the aortic arch; and including keeping said second balloon inflated during a plurality of periods when said balloon which lies in the ascending aorta is deflated.

17. Apparatus for use in resuscitating a person who has suffered cardiac arrest, comprising:

a mechanism which is operable to at least partially block and then to reduce the blockage, of the ascending aorta of the person;

a control circuit coupled to said mechanism, said circuit being constructed to operate said mechanism to block the ascending aorta for a period which has a duration of more than one second, to cause a larger than normal portion of blood pumped from the left ventricle to flow to the coronary arteries, to then operate said mechanism to reduce the blockage of the ascending aorta for a period of a plurality of seconds to allow some pumped blood to flow to the brain, and then to again operate said mechanism to block the ascending aorta for a period of more than one second.

* * * * *